(12) United States Patent
Nelson et al.

(10) Patent No.: US 10,933,151 B2
(45) Date of Patent: Mar. 2, 2021

(54) PLASMA STERILIZATION SYSTEM AND METHODS

(71) Applicant: 3M INNOVATIVE PROPERTIES COMPANY, St. Paul, MN (US)

(72) Inventors: Caleb T. Nelson, Woodbury, MN (US); Assumpta A. G. Bennaars-Eiden, Woodbury, MN (US); Matthew T. Scholz, Woodbury, MN (US); Petra L. Kohler Riedi, Minneapolis, MN (US); Steven P. Swanson, Blaine, MN (US); Nardine S. Abadeer, Columbus, OH (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 159 days.

(21) Appl. No.: 16/307,302

(22) PCT Filed: Jun. 29, 2017

(86) PCT No.: PCT/US2017/039856
§ 371 (c)(1),
(2) Date: Dec. 5, 2018

(87) PCT Pub. No.: WO2018/005715
PCT Pub. Date: Jan. 4, 2018

(65) Prior Publication Data
US 2019/0134243 A1    May 9, 2019

Related U.S. Application Data

(60) Provisional application No. 62/357,158, filed on Jun. 30, 2016, provisional application No. 62/525,582, filed on Jun. 27, 2017.

(51) Int. Cl.
*A61L 2/00* (2006.01)
*B01J 19/08* (2006.01)
(Continued)

(52) U.S. Cl.
CPC .............. *A61L 2/14* (2013.01); *H05H 1/2406* (2013.01); *H05H 2001/245* (2013.01); *H05H 2245/1225* (2013.01)

(58) Field of Classification Search
CPC ..... A61L 2/00; A61L 2/03; A61L 2/14; A61L 2202/00
(Continued)

(56) References Cited

U.S. PATENT DOCUMENTS 3,054,270 A    9/1962    Huston
3,564,861 A    2/1971    Andersen
(Continued)

FOREIGN PATENT DOCUMENTS

CA    2042283    11/1991
CA    2042284    11/1991
(Continued)

OTHER PUBLICATIONS

Joshi, "Control of methicillin-resistant *Staphylococcus aureus* in planktonic form and biofilms: A biocidal efficacy study of nonthermal dielectric-barrier discharge plasma". American Journal of Infection Control, 2010. vol. 38, No. 4, pp. 293-301.
(Continued)

*Primary Examiner* — Monzer R Chorbaji
(74) *Attorney, Agent, or Firm* — James A. Baker (57) ABSTRACT

A system and methods for sterilizing or disinfecting articles, particularly the hollow internal areas of medical instruments are disclosed. The system includes a plasma generator having an electrode, a shield, and a dielectric gap between the electrode and the shield. A source of electrical power is connected to the plasma generator for applying an electron energy density between the electrode and the shield. A source of gas comprising water vapor, oxygen and nitrogen provides a flow of gas between the electrode and the shield, (Continued)

to form a plasma containing acidic and/or oxidizing species. In the exemplary system, the temperature at the shield's surface is <150° C. when the electron energy density is >0.05 eV/molecule of the gas. Also disclosed is a method for disinfecting an article contaminated with a bio-film or spores, by exposing the contaminated article to the plasma for an exposure time sufficient to achieve at least 2-$\log_{10}$ reduction in colony forming units.

18 Claims, 2 Drawing Sheets

(51) Int. Cl.
*A61L 2/14* (2006.01)
*H05H 1/24* (2006.01)

(58) Field of Classification Search
USPC .................................. 422/22, 186.04, 186.05
See application file for complete search history.

(56) References Cited

U.S. PATENT DOCUMENTS

| | | | |
|---|---|---|---|
| 3,571,563 A | 3/1971 | Shulz | |
| 4,294,804 A | 10/1981 | Baran | |
| 4,301,113 A | 11/1981 | Alguire | |
| 5,317,986 A | 6/1994 | Blanes | |
| 5,399,314 A | 3/1995 | Samuel | |
| 2002/0070025 A1 | 6/2002 | McIntosh | |
| 2003/0015505 A1 | 1/2003 | Yu et al. | |
| 2003/0029566 A1 | 2/2003 | Roth | |
| 2004/0037736 A1* | 2/2004 | Perruchot | A61L 2/14 422/22 |
| 2004/0084812 A1 | 5/2004 | Grunwald | |
| 2005/0269199 A1 | 12/2005 | Pollak | |
| 2008/0292497 A1 | 11/2008 | Vangeneugden et al. | |
| 2011/0009535 A1 | 1/2011 | Mikumo | |
| 2012/0063966 A1 | 3/2012 | Liao | |
| 2012/0183437 A1 | 7/2012 | Keener | |
| 2013/0053760 A1 | 2/2013 | Ehlbeck | |
| 2013/0142694 A1 | 6/2013 | Krohmann | |
| 2013/0156641 A1 | 6/2013 | Paskalov | |

FOREIGN PATENT DOCUMENTS

| | | |
|---|---|---|
| CN | 101284142 | 10/2008 |
| EP | 2153851 | 2/2010 |
| WO | WO 2011-087544 | 7/2011 |
| WO | WO 2013-167862 | 11/2013 |
| WO | WO 2014/057409 A2 | 4/2014 |

OTHER PUBLICATIONS

Kobayashi, "Decrease in Ozone Density of Atmospheric Surface Discharge Plasma Source", Japanese journal of applied physics, 2012, vol. 51, No. 8, pp. 08HC0401-04.

Kunapareddy,"Evaluation of Dieletric Barrier Discharge Sterilization of *Escherichia coli* with a Swept—Wavelength Resonance—Raman Device" Plasma Medicine, 2011, pp. 231-240.

McCombs, "New discoveries and directions for medical, dental and dental hygiene research: low temperature atmospheric pressure plasma" International Journal of Dental Hygiene 8, 2010, pp. 10-15.

Shimizu, "Basic study of remote disinfection and sterilization effect by using atmospheric microplasma" IEEE Transactions on industry applications,2012, vol. 48, No. 4, pp. 1182-1188.

Shintani, "Gas plasma sterilization of microorganisms and mechanisms of action", Experimental and therapeutic medicine, 2010, vol. 1, pp. 731-738.

International Search report for PCT International Application No. PCT/US2017/039856 dated Oct. 2, 2017, 7 pages.

* cited by examiner

PLASMA STERILIZATION SYSTEM AND METHODS

Cross Reference to Related Applications

This application is a national stage filing under 35 U.S.C. 371 of PCT/US2017/039856, filed Jun. 29, 2017, which claims the benefit of U.S. Application No. 62/357,158, filed Jun. 30, 2016; and U.S. Application No. 62/525,582, filed Jun. 27, 2017, the disclosure of which is incorporated by reference in its/their entirety herein.

FIELD

The present disclosure relates generally to the sterilization or disinfection of medical apparatus and articles, and more particularly to the application of a gas plasma with reactive species to effect sterilization or disinfection of medical articles such as medical instruments or medical endoscope lumens.

BACKGROUND

A reliable supply of sterile apparatus, instruments and supplies is vitally important to modem medical practice. Various types of apparatus are known for sterilizing reusable goods within a hospital setting including, for example, steam autoclaves. U.S. Pat. No. 4,301,113 (Alguire et al); U.S. Pat. No. 4,294,804 (Baran); U.S. Pat. No. 5,317,896 (Sheth et al); U.S. Pat. No. 5,399,314 (Samuel et al); U.S. Pat. No. 3,571,563 (Shulz); U.S. Pat. No. 3,054,270 (Huston); and U.S. Pat. No. 3,564,861 (Andersen et al), discuss sterilization apparatus and their control systems. Goods which cannot withstand autoclaving temperatures can be sterilized with sterilizers using a biocidal gas such as ethylene oxide.

Although ethylene oxide is an excellent sterilizant and penetrates well into the lumens of, e.g., endoscopes, ethylene oxide also exhibits undesirable toxicity and flammability, and for at least these reasons, the art has sought alternatives.

SUMMARY

The present disclosure provides a sterilization or disinfection system employing an oxygen/nitrogen plasma as the sterilizing gas. The disclosed embodiments permit a high electrode energy density while minimizing unwanted heat production.

In one aspect, the present disclosure relates to a system including a plasma generator. The plasma generator includes an electrode, a shield, and a dielectric gap between the electrode and the shield. A source of electrical power is connected to the plasma generator for applying an electrode energy density between the electrode and the shield. A source of gas provides a gas flow through the plasma generator to form from the gas a plasma containing acidic and/or oxidizing species. The system may also include a device for conveying an article undergoing sterilization through a chamber fluently connected to the source of the gas.

In exemplary embodiments of the system, the gas includes one or more species selected from the group consisting of molecular oxygen, molecular nitrogen, nitric oxide, nitric acid, and nitrous oxide. Preferably, the gas includes water vapor, molecular oxygen, and molecular nitrogen. In some exemplary embodiments, the gas comprises air. Preferably, the relative humidity of the gas entering the plasma generator is at least 21%.

In certain presently preferred embodiments, the temperature at the surface of the shield is preferably maintained at less than 150° C. when the electrode energy density is greater than 0.05 eV/molecule of the gas passing between the electrode and the shield. In some exemplary embodiments, the source of electrical power is a pulsed DC source having a high dV/dT. In certain exemplary embodiments, the system further includes a cooling apparatus. In some exemplary embodiments, the system includes a filter for removing the acidic and/or oxidizing species from the gas.

In a second aspect, the present disclosure describes a method for sterilizing a contaminated article using a sterilizer including a plasma generator having an electrode, a shield, and a dielectric gap between the electrode and the shield, a source of electrical power connected to the plasma generator for applying an electrode energy density between the electrode and the shield, and a source of gas providing a flow through the plasma generator to form a plasma containing acidic and/or oxidizing species from the gas. The gas containing the acidic and/or oxidizing species is directed from the plasma generator into an enclosed area including the portions of the article undergoing sterilization.

In exemplary embodiments, the gas includes water vapor, oxygen, and nitrogen, and the temperature at the surface of the shield is maintained at less than 150° C. when the electrode energy density is greater than 0.05 eV/molecule of the gas passing between the electrode and the shield. The contaminated article is exposed to the gas containing the acidic and/or oxidizing species for an exposure time sufficient to sterilize the contaminated article, which is preferably no more than one hour.

In a third aspect, the present disclosure describes a method of disinfecting a contaminated article, including providing a disinfecting system having a plasma generator having an electrode, a shield, and a dielectric gap between the electrode and the shield, a source of electrical power connected to the plasma generator for applying an electrode energy density between the electrode and the shield, and a source of a gas comprising water vapor, oxygen, and nitrogen, configured to provide a flow of the gas through the plasma generator between the electrode and the shield to form a plasma containing acidic and/or oxidizing species from the gas. The gas containing the acidic and/or oxidizing species is directed from the plasma generator into an enclosed area including the portions of the article undergoing disinfection.

In some exemplary embodiments, the contaminated article is contaminated with at least one of a bio-film comprising a plurality of microorganisms, or a plurality of microbial or fungal spores. The contaminated article is exposed to the gas containing the acidic and/or oxidizing species for an exposure time sufficient to disinfect the contaminated article by achieving at least a 2-$\log_{10}$ and optionally up to an 11-$\log_{10}$ reduction in colony forming units of the disinfected contaminated article relative to the contaminated article.

Additional exemplary embodiments within the scope of the present disclosure are provided in the following Listing of Exemplary Embodiments.

Listing of Exemplary Embodiments

A. A system, comprising:
a plasma generator including:
  an electrode,
  a shield, and
  a dielectric gap between the electrode and the shield;
a source of electrical power connected to the plasma generator, for applying an electrode energy density between the electrode and the shield; and
a source of a gas comprising water vapor, oxygen, and nitrogen, configured to provide a flow of the gas through the plasma generator between the electrode and the shield to form a plasma containing acidic and/or oxidizing species from the gas; wherein
a temperature at the surface of the shield is maintained at less than 150° C. when the electrode energy density is greater than 0.05 eV/molecule of the gas passing between the electrode and the shield, optionally wherein the system further comprises a device for conveying an article undergoing sterilization through a chamber fluently connected to the flow of the gas through the plasma generator containing the acidic and/or oxidizing species.

B. The system of Embodiment A, wherein the gas includes one or more species selected from the group consisting of molecular oxygen, molecular nitrogen, nitric oxide, nitric acid, and nitrous oxide.

C. The system of Embodiment B, wherein the gas comprises air.

D. The system of any one of Embodiments A to C, wherein a relative humidity of the gas entering the plasma generator is at least 21%.

E. The system of any one of Embodiments A to D, further comprising a cooling apparatus.

F. The system of any one of Embodiments A to E, wherein the source of electrical power is a pulsed DC source having a high dV/dT.

G. The system of any one of Embodiments A to F, further comprising a filter for removing the acidic and/or oxidizing species from the gas.

H. A method of sterilizing a contaminated article, comprising:
providing a sterilizer including:
  a plasma generator having:
    an electrode,
    a shield, and
    a dielectric gap between the electrode and the shield;
  a source of electrical power connected to the plasma generator for applying an electrode energy density between the electrode and the shield; and
  a source of a gas comprising water vapor, oxygen, and nitrogen, configured to provide a flow of the gas through the plasma generator between the electrode and the shield to form a plasma containing acidic and/or oxidizing species from the gas;
providing the flow of the gas through the plasma generator between the electrode and the shield to form the plasma containing the acidic and/or oxidizing species from the gas, wherein a temperature at the surface of the shield is maintained at less than 150° C. when the electrode energy density is greater than 0.05 eV/molecule of the gas passing between the electrode and the shield;
directing the gas containing the acidic and/or oxidizing species from the plasma generator into an enclosed area enclosing at least a portion of the article undergoing sterilization to achieve a desired degree of sterilization of the article; and
exposing the contaminated article to the gas containing the acidic and/or oxidizing species for a time sufficient to sterilize the contaminated article, optionally wherein the time sufficient to sterilize the article is no greater than one hour.

I. The method of Embodiment H, further comprising removing at least a portion of the acidic and/or oxidizing species from the gas upon achieving the desired degree of sterilization of the article.

J. The method of Embodiment I, wherein the removing at least a portion of the acidic and/or oxidizing species from the gas is performed with an apparatus comprising one or more materials selected from the group consisting of activated carbon, a species with a basic functionality, a species providing a basic adsorbent, a reducing species, and a molecular sieve.

K. The method of Embodiment I, wherein the removing is performed by directing the gas through a catalytic reducer.

L. The method of any one of Embodiments H to K, wherein the enclosed area is a sterilization chamber.

M. The method of any one of Embodiments H to K, wherein the article undergoing sterilization is a medical device and the enclosed area is a hollow area of the medical device.

N. The method of Embodiment M, wherein the medical device is an endoscope and the hollow area is a lumen of the endoscope, further wherein the gas containing the acidic and/or oxidizing species from the plasma generator is passed through the lumen of the endoscope.

O. The method of claim Embodiment M, wherein the medical device is a medical instrument and the hollow area is at least one internal cavity of the medical instrument.

P. The method of any one of Embodiments H to O, wherein the gas includes one or species selected from the group consisting of molecular oxygen, molecular nitrogen, nitric oxide, nitric acid, and nitrous oxide.

Q. The method of Embodiment P, wherein the gas comprises air.

R. The method of any Embodiments H to Q, wherein a relative humidity of the gas entering the plasma generator is at least 21%.

S. The method of any one of Embodiments H to R, further comprising a cooling apparatus.

T. The method of any one of Embodiments H to S, wherein the source of electrical power is a pulsed DC source having a high dV/dT.

U. A method of disinfecting a contaminated article, comprising:
providing a disinfecting system including:
  a plasma generator having:
    an electrode,
    a shield, and
    a dielectric gap between the electrode and the shield,
  a source of electrical power connected to the plasma generator for applying an electrode energy density between the electrode and the shield, and
  a source of a gas comprising water vapor, oxygen, and nitrogen, configured to provide a flow of the gas through the plasma generator between the electrode and the shield to form a plasma containing acidic and/or oxidizing species from the gas;
providing the flow of the gas through the plasma generator between the electrode and the shield to form the plasma containing the acidic and/or oxidizing species from the gas;
directing the gas containing the acidic and/or oxidizing species from the plasma generator into an enclosed area enclosing at least a portion of the contaminated article, wherein the contaminated article is contaminated with at least one of a bio-film comprising a plurality of microorganisms, or a plurality of microbial or fungal spores; and exposing the contaminated article to the gas containing the acidic and/or oxidizing species for an exposure time sufficient to disinfect the contaminated article by achieving at least a 2-$\log_{10}$ and optionally up to an 11-$\log_{10}$ reduction in colony forming units of the disinfected contaminated article relative to the contaminated article.

V. The method of Embodiment U, wherein the contaminated article is a medical device and the enclosed area is a hollow area of the medical device.

W. The method of Embodiment V, wherein the medical device is an endoscope and the hollow area is a lumen of the endoscope, further wherein the gas containing the acidic and/or oxidizing species from the plasma generator is passed through the lumen of the endoscope.

X. The method of any one of Embodiments U to W, wherein the bio-film comprises a plurality of microorganisms selected from the group consisting of *Geobacillus stearothermophilus, Bacillus subtilis, Bacillus atrophaeus, Bacillus megaterium, Bacillus coagulans, Clostridium sporogenes, Bacillus pumilus, Aspergillus brasiliensis, Aspergillus oryzae, Aspergillus niger, Aspergillus nidulans, Aspergillus flavus, Clostridium difficile, Mycobacterium terrae, Mycobacterium tuberculosis, Mycobacterium bovis, Escherichia coli, Staphylococcus aureus, Pseudomonas aeruginosa, Staphylococcus epidermidis, Staphyolococcus lugdunensis, Staphylococcus saprophyticus, Enterococcus faecium, Enterococcus faecalis, Propionobacterium acnes, Klebsiella pneumoniae, Enterobacter cloacae, Proteus mirabilus, Salmonella enterica, Salmonella typhi, Shigella flexiniri*, and combinations thereof.

Y. The method of any one of Embodiments U to X, wherein the contaminated article is contaminated with a bio-film comprising a plurality of microorganisms, further wherein the exposure time is at least 5 minutes, and the reduction in colony forming units of the disinfected article relative to the contaminated article is from 4-$\log_{10}$ to 9-$\log_{10}$, optionally wherein the exposure time is at most one hour.

Z. The method of any one of Embodiments U to X, wherein the contaminated article is contaminated with a bio-film comprising a plurality of microbial or fungal spores, further wherein the exposure time is at least 2 minutes, and the reduction in colony forming units of the disinfected article relative to the contaminated article is from 6-$\log_{10}$ to 10-$\log_{10}$, optionally wherein the exposure time is at most one hour.

AA. The method of any one of Embodiments U to Z, wherein the gas includes at least one species selected from the group consisting of molecular oxygen, molecular nitrogen, nitric oxide, nitric acid, and nitrous oxide.

BB. The method of Embodiment AA, wherein the gas comprises air.

CC. The method of any one of Embodiments U to BB, wherein the temperature at a surface of the shield is maintained at less than 150° C. when the electrode energy density is greater than 0.05 eV/molecule of the gas passing between the electrode and the shield, optionally wherein a relative humidity of the gas entering the plasma generator is at least 21%.

DD. The method of any one of Embodiments U to CC, further comprising removing the acidic and/or oxidizing species from the gas.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

The present disclosure describes an apparatus and methods for sterilizing or disinfecting articles using a gas plasma including oxygen, nitrogen, and reactive species produced from these gases. In some convenient embodiments, the plasma is directed to a chamber in which the goods to be sterilized or disinfected are placed. In other convenient embodiments, the plasma is directed into the lumen of an apparatus or article requiring sterilization or disinfection.

Glossary

Certain terms are used throughout the description and the claims that, while for the most part are well known, may require some explanation. It should understood that, as used herein unless a different definition is expressly provided in the claims or elsewhere in the specification, including the drawings:

The terms "about" or "approximately" with reference to a numerical value or a shape means +/−five percent of the numerical value or property or characteristic, but expressly includes the exact numerical value. For example, a viscosity of "about" 1 Pa-sec refers to a viscosity from 0.95 to 1.05 Pa-sec, but also expressly includes a viscosity of exactly 1 Pa-sec.

As used in this specification and the appended embodiments, the singular forms "a", "an", and "the" include plural referents unless the content clearly dictates otherwise. Thus, for example, reference to fine fibers containing "a compound" includes a mixture of two or more compounds. As used in this specification and the appended embodiments, the term "or" is generally employed in its sense including "and/or" unless the content clearly dictates otherwise.

The term "substantially" with particular reference to a property or characteristic means that the property or characteristic is exhibited to a greater extent than the opposite of that property or characteristic is exhibited. For example, a substrate that is "substantially" transparent refers to a substrate that transmits more radiation (e.g. visible light) than it fails to transmit (e.g. absorbs and reflects). Thus, a substrate that transmits more than 50% of the visible light incident upon its surface is substantially transparent, but a substrate that transmits 50% or less of the visible light incident upon its surface is not substantially transparent.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Exemplary embodiments of the present disclosure may take on various modifications and alterations without departing from the spirit and scope of the present disclosure. Accordingly, it is to be understood that the embodiments of the present disclosure are not to be limited to the following described exemplary embodiments, but is to be controlled by the limitations set forth in the claims and any equivalents thereof.

Exemplary Sterilizing Apparatus and Processes

Various exemplary embodiments of the disclosure will now be described with particular reference to the Drawings.

The present disclosure describes a sterilization or disinfection system including a plasma generator. The plasma generator includes an electrode, a shield, and a dielectric gap between the electrode and the shield. A source of electrical power is connected to the plasma generator for applying an electrode energy density between the electrode and the shield. A source of gas provides a gas flow through the plasma generator to form from the gas a plasma containing acidic and/or oxidizing species. The system may also include a device for conveying an article undergoing sterilization through a chamber fluently connected to the source of the gas.

In exemplary embodiments of the sterilization/disinfection system, the gas includes one or more species selected from the group consisting of molecular oxygen, molecular nitrogen, nitric oxide, nitric acid, and nitrous oxide. Preferably, the gas includes water vapor, molecular oxygen, and molecular nitrogen. In some exemplary embodiments, the gas comprises air. Preferably, the relative humidity of the gas entering the plasma generator is at least 21%.

In certain presently preferred embodiments, the temperature at the surface of the shield is preferably maintained at less than 150° C. when the electrode energy density is greater than 0.05 eV/molecule of the gas passing between the electrode and the shield. In some exemplary embodiments, the source of electrical power is a pulsed DC source having a high dV/dT. In certain exemplary embodiments, the system further includes a cooling apparatus. In some exemplary embodiments, the system includes a filter for removing the acidic and/or oxidizing species from the gas.

Figure 1:
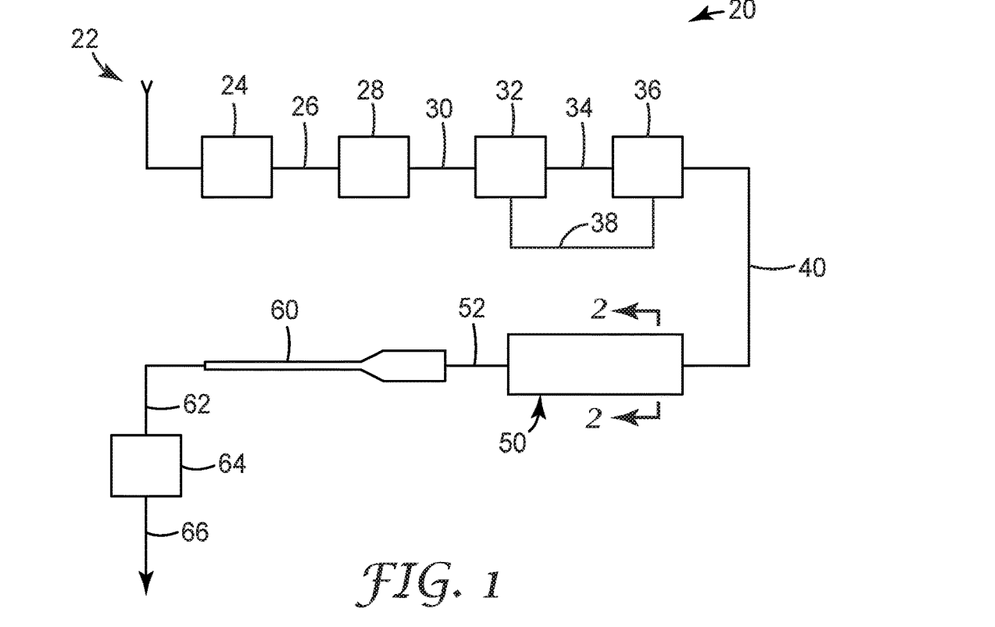
FIG. 1 is a schematic view of an exemplary sterilization system of the present disclosure.

Referring now to FIG. 1, a schematic view of an exemplary sterilization or disinfection system 20 of the present disclosure is illustrated. Sterilization/disinfection system 20 includes a source of gas 22, which comprises molecular oxygen and nitrogen. The gas from source 22 may be air or a specific blend including molecular oxygen and nitrogen at a specified ratio, and may be pressurized or unpressurized as provided. If from an unpressurized source 22, a compressor 24 may be used to pressurize the gas to a convenient pressure. The gas is then transported via line 26 to a flow controller 28 to meter the mass flow of gas to the rest of the sterilization system 20. Flow controller 26 may take the form of a pressure regulator, a ball-in-tube flowmeter, an electronic mass flow controller, or other similar device.

The gas is then transported via line 30 to a humidification device 32 to bring the humidity of the gas to between about 1 and 50 g/m³, between 2 and 40 g/m³, between 3 and 30 g/m³, between 4 and 20 g/m³, or even between 5 and 15 g/m³. Diverse expedients such a bubblers, spargers, atomizers, and wick-type humidifiers are all suitable. In the depicted embodiment, the humidified gas is conveyed via line 34 to an optional humidity detector 36 to verify that the humidity level is within the desired range. In some convenient embodiments, feedback control via control line 38 is provided to manipulate humidification device 30 appropriately.

The humidified gas is transported via line 40 to a plasma generator 50, which will be discussed with more particularity below. Plasma generator 50 induces the production of diverse chemical species in the humidified gas, including one or more of nitrous acid, nitric acid, ozone, and nitrous oxide. This gas is conveyed to a remote location by line 52. Surprisingly, line 52 may be quite long without losing sterilizing efficacy: distances between about 0.5 to 90 meters have been found to be suitable.

Line 52 may, for example deliver sterilizing/disinfecting gas directly to an endoscope 60 or another lumen-containing device to sterilize the internal lumen. Gas leaves the endoscope 60 via line 62 and is conveyed to a filter 64 to render the gas harmless. In convenient embodiments, the filter 64 will include an alkaline element such as sodium bicarbonate to neutralize any remaining acidic species. An element such as activated carbon to remove oxidizing species such as ozone is also conveniently present. After filtration, the gas can be released to ambient via outlet 66.

Figure 2A:
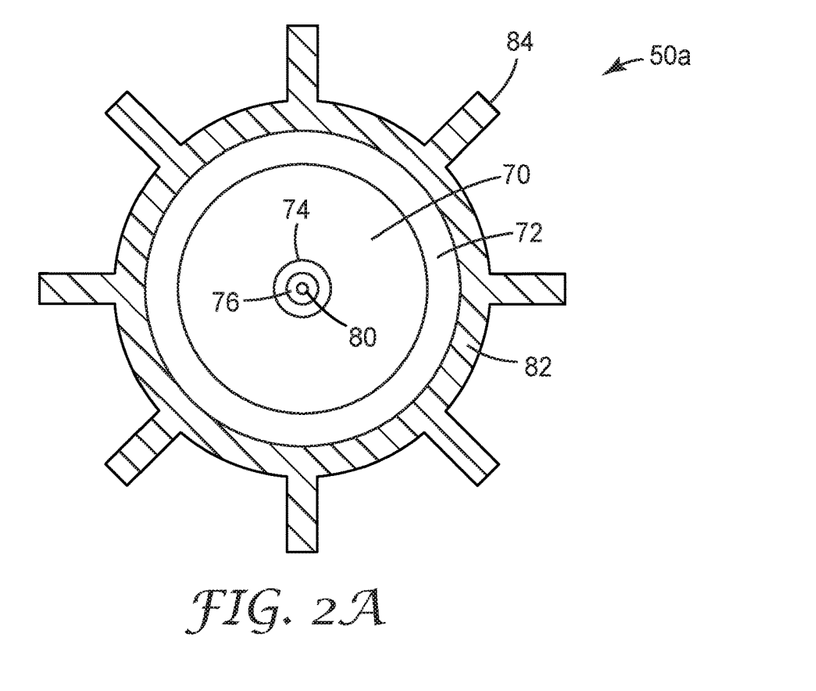
FIG. 2A is a cross-section view of one variant of a plasma generator taken along section lines 2-2 in FIG. 1.

Referring now to FIG. 2A, a cross-section view of one variant 50a of plasma generator 50 taken along section lines 2-2 in FIG. 1 is illustrated. In variant 50a, the gas is conveyed through lumen 70 in outer tube 72. Tube 72 is a dielectric, conveniently glass. Within lumen 70 is inner tube 74 having a lumen 76. Tube 74 is also a dielectric, conveniently glass. Within lumen 76 is first electrode 80. A second electrode 82 surrounds the outer tube 72, and in some convenient embodiments has heat radiating fins 84 so that it serves additional duty as a heat sink. Other expedients may be used to provide cooling, such as a fan, fins, heat exchanger, piezoelectric cooling, and combinations thereof.

During operation, a potential difference must exist between first electrode 80 and second electrode 82. In some convenient embodiments, first electrode 80 is the high voltage electrode and second electrode 82 is the ground electrode. An AC voltage of between about 4 to 12 kV is conveniently applied to first electrode 80, having a frequency of between about 4 to 30 kHz. The exact conditions depend on the gas flow needed to efficaciously treat the apparatus needing sterilization, the available cooling capacity for plasma generator 50, and the dimension of the outer and inner tubes 72 and 74 respectively. In any case, the electrical parameters must cause the conditions to exceed the breakdown voltage of the gas between the tubes.

Figure 2B:
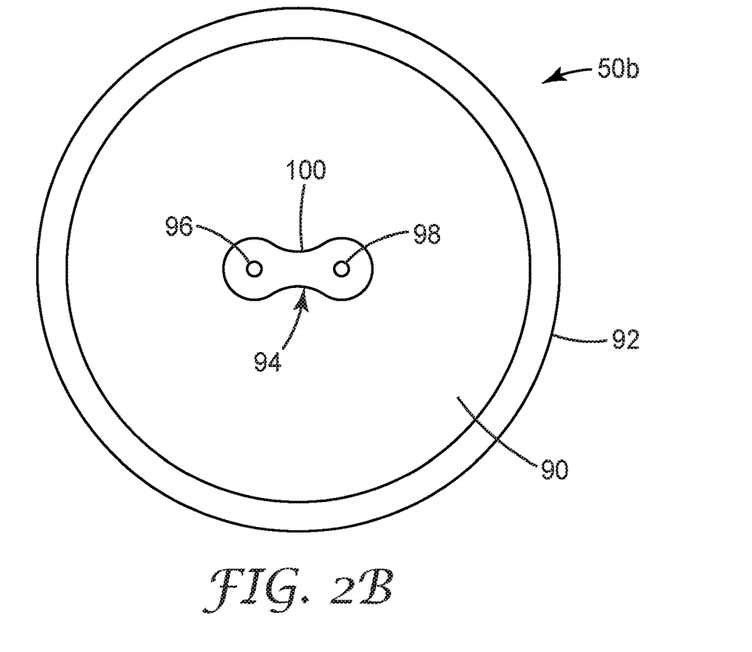
FIG. 2B is a cross-section view of another variant of a plasma generator taken along section lines 2-2 in FIG. 1.

Referring now to FIG. 2B, a cross-section view of another variant 50b of plasma generator 50 taken along section lines 2-2 in FIG. 1 is illustrated. In variant 50b, the gas is conveyed through lumen 90 in tube 92. Tube 92 is conveniently polymeric tubing such a polytetrafluoroethylene (PTFE). Also within lumen 90 is, e.g. a ribbon cable 94 including a first conductor 96, a second conductor 98, conveniently both within a dielectric insulation 100.

Figure 2C:
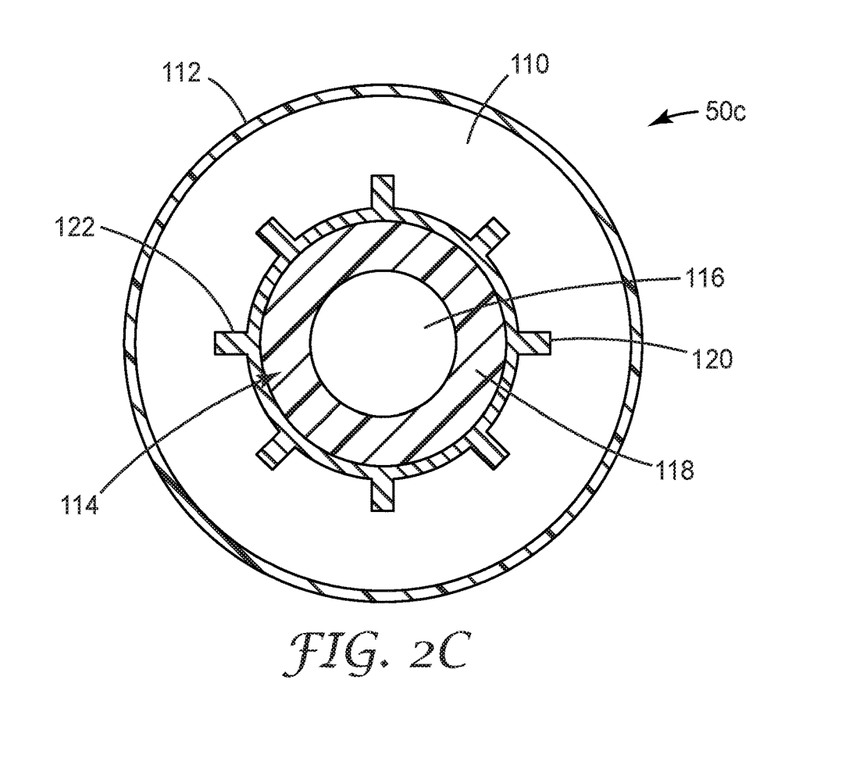
FIG. 2C is a cross-section view of another variant of a plasma generator taken along section lines 2-2 in FIG. 1.

Referring now to FIG. 2C, a cross-section view of one variant 50c of plasma generator 50 taken along section lines 2-2 in FIG. 1 is illustrated. In variant 50c, the gas is conveyed through lumen 110 in tube 112. Tube 112 is conveniently polymeric tubing such a polytetrafluoroethylene (PTFE). Also within lumen 110 is electrode subassembly 114, comprising electrode 116, conveniently the high voltage electrode, surrounded by a dielectric layer 118. Around dielectric layer 118 is another electrode 120, conveniently the ground electrode. Fins 122 be conveniently be present to improve the electric field being generated.

During operation, a potential difference should exist first conductor 96 and second conductor 98. In some convenient embodiments, first conductor 96 is the high voltage electrode and second conductor 98 is the ground electrode. A DC voltage of at least 20 kV, at least 30 kV, at least 40 kV, and even at least 50 kV, but preferably no more than 100 kV, 90 kV, 80 kV, 70 kV, or even 60 kV, is conveniently applied to first conductor 96 in pulses having a duration on the order of nanoseconds with an extremely fast dV/dt. By this it is meant that the rise of the pulse the highest instantaneous rate of change of the voltage should reach a rate of at least 10 kV/nano-sec, at least 20 kV/nano-sec, at least 30 kV/nano-sec, at least 40 kV/nano-sec, or even at least 50 kV/nano-sec. This type of charging allows plasma to be generated within the gas with relatively little heating.

Other exemplary embodiments of the present disclosure describe a method for sterilizing a contaminated article using a sterilization system as previously described. The sterilization system includes a plasma generator having an electrode, a shield, and a dielectric gap between the electrode and the shield, a source of electrical power connected to the plasma generator for applying an electrode energy density between the electrode and the shield, and a source of gas providing a flow through the plasma generator to form a plasma containing acidic and/or oxidizing species from the gas. The gas containing the acidic and/or oxidizing species is directed from the plasma generator into an enclosed area including the portions of the article undergoing sterilization.

In certain presently-preferred embodiments, the gas includes water vapor, oxygen, and nitrogen, and the temperature at the surface of the shield is maintained at less than 150° C. when the electrode energy density is greater than 0.05 eV/molecule of the gas passing between the electrode and the shield. The contaminated article is exposed to the gas containing the acidic and/or oxidizing species for an exposure time sufficient to sterilize the contaminated article, which is preferably no more than one hour.

In certain exemplary embodiments, the method further includes removing at least a portion of the acidic and/or oxidizing species from the gas upon achieving the desired degree of sterilization of the article. Removing the acidic and/or oxidizing species from the gas may be performed with an apparatus including one or more adsorbent or absorbent materials selected from activated carbon, a chemical species with a basic functionality (e.g., an organic amine, sodium hydroxide, potassium hydroxide, lithium hydroxide, and the like), a species providing a basic adsorbent (e.g. a basic ion exchange resin), a reducing species (e.g., one or more active metals such as platinum, palladium, and the like), and a molecular sieve. In some exemplary embodiments, removing the acidic and/or oxidizing species from the gas may be performed by directing the gas through a catalytic reducer.

In further exemplary embodiments, the enclosed area is a sterilization chamber. In other exemplary embodiments, the article undergoing sterilization is a medical device and the enclosed area is a hollow area of the medical device. In some presently-preferred embodiments, the medical device is an endoscope and the hollow area is the lumen of the endoscope, and the gas containing the acidic and/or oxidizing species from the plasma generator is passed through the lumen of the endoscope.

In other exemplary embodiments, the medical device is a medical instrument and the hollow area is at least one internal cavity of the medical instrument.

Certain embodiments of the present disclosure also describes a method of disinfecting a contaminated article, including providing a disinfecting system having a plasma generator having an electrode, a shield, and a dielectric gap between the electrode and the shield, a source of electrical power connected to the plasma generator for applying an electrode energy density between the electrode and the shield, and a source of a gas comprising water vapor, oxygen, and nitrogen, configured to provide a flow of the gas through the plasma generator between the electrode and the shield to form a plasma containing acidic and/or oxidizing species from the gas. The gas containing the acidic and/or oxidizing species is directed from the plasma generator into an enclosed area including the portions of the article undergoing disinfection.

In some exemplary embodiments, the contaminated article is contaminated with at least one of a bio-film comprising a plurality of microorganisms, or a plurality of microbial or fungal spores. The contaminated article is exposed to the gas containing the acidic and/or oxidizing species for an exposure time sufficient to disinfect the contaminated article by achieving at least a 2-$\log_{10}$ and optionally up to an 11-$\log_{10}$ reduction in colony forming units of the disinfected contaminated article relative to the contaminated article.

In certain such exemplary embodiments, the article undergoing sterilization is a medical device and the enclosed area is a hollow area of the medical device. In some presently-preferred embodiments, the medical device is an endoscope and the hollow area is the lumen of the endoscope, and the gas containing the acidic and/or oxidizing species from the plasma generator is passed through the lumen of the endoscope.

In some exemplary embodiments the bio-film comprises a plurality of microorganisms selected from spores such as, for example, *Geobacillus stearothermophilus, Bacillus subtilis, Bacillus atrophaeus, Bacillus megaterium, Bacillus coagulans, Clostridium sporogenes, Bacillus pumilus, Aspergillus brasiliensis, Aspergillus oryzae, Aspergillus niger, Aspergillus nidulans, Aspergillus flavus, Clostridium difficile;* bacterial cells such as, for example, *Mycobacterium terrae, Mycobacterium tuberculosis,* and *Mycobacterium*

*bovis;* and biofilm-forming bacteria such as, for example *Escherichia coli, Staphylococcus aureus, Pseudomonas aeruginosa, Staphylococcus epidermidis, Staphyolcoccus lugdunensis, Staphylococcus saprophyticus, Enterococcus faecium, Enterococcus faecalis, Propionobacterium acnes, Klebsiella pneumoniae, Enterobacter cloacae, Proteus mrabilus, Salmonella enterica, Salmonella typhi,* and *Shigella flexiniri;* as well as any combination thereof.

In certain exemplary embodiments, the contaminated article is contaminated with a bio-film including a plurality of microorganisms, the exposure time is at least 5 minutes, and the reduction in colony forming units of the disinfected article relative to the contaminated article is from 4-$\log_{10}$ to 9-$\log_{10}$. More preferably, the reduction in colony forming units of the disinfected article relative to the contaminated article is from 5-$\log_{10}$ to 9-$\log_{10}$; from 6-$\log_{10}$ to 9-$\log_{10}$; or even from 6-$\log_{10}$ to 9-$\log_{10}$.

Preferably, the exposure time to achieve the desired level of disinfection of the contaminated article contaminated with a bio-film including a plurality of microorganisms, is selected to be at most one hour. More preferably, the exposure time to achieve the desired level of disinfection is no greater than 50 minutes, 40 minutes, 30 minutes, 20 minutes, or even 10 minutes. Most preferably, the exposure time to achieve the desired level of disinfection is selected to be at most 9 minutes, 8 minutes, 7 minutes, 6 minutes, 5 minutes, or as low as 4 minutes, 3 minutes, two minutes, or even 1 minute In other exemplary embodiments, the contaminated article is contaminated with a bio-film including a plurality of microbial or fungal spores, the exposure time is at least 2 minutes, and the reduction in colony forming units of the disinfected article relative to the contaminated article is from 6-$\log_{10}$ to 10-$\log_{10}$. More preferably, the reduction in colony forming units of the disinfected article relative to the contaminated article is from 7-$\log_{10}$ to 10-$\log_{10}$; from 8-$\log_{10}$ to 10-$\log_{10}$; or even from 9-$\log_{10}$ to10-$\log_{10}$.

Preferably, the exposure time to achieve the desired level of disinfection of the contaminated article contaminated with a bio-film including a plurality of microbial or fungal spores is selected to be at most one hour. More preferably, the exposure time to achieve the desired level of disinfection is no greater than 50 minutes, 40 minutes, 30 minutes, 20 minutes, or even 10 minutes. Most preferably, the exposure time to achieve the desired level of disinfection is selected to be at most 9 minutes, 8 minutes, 7 minutes, 6 minutes, 5 minutes, or as low as 4 minutes, 3 minutes, two minutes, or even 1 minute The operation of exemplary embodiments of the present disclosure will be further described with respect to the following non-limiting detailed Examples. These examples are offered to further illustrate the various specific and preferred embodiments and techniques. It should be understood, however, that many variations and modifications may be made while remaining within the scope of the present disclosure.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Materials

Unless otherwise noted, all parts, percentages, ratios, etc. in the Examples and the rest of the specification are by weight. Solvents and other reagents used may be obtained from Sigma-Aldrich Chemical Company (Milwaukee, Wis.) unless otherwise noted. In addition, Table 1 provides abbreviations and a source for all materials used in the Examples below:

TABLE 1

Materials

| Materials | Source |
|---|---|
| Phosphate buffered saline 10X concentrate P5493-1L | Sigma Aldrich, St Louis, MO |
| TWEEN 80 (P4780) | Sigma Aldrich, St Louis, MO |
| 3M ™ Petrifilm ™ Aerobic Count Plates (6400) | 3M Company, St. Paul, MN |
| 3M ™ Petrifilm ™ Plate Reader (6499) | 3M Company, St. Paul, MN |
| Mini Flip Top Vial With Butterfields Buffer | 3M Company, St. Paul, MN |
| Polytetrafluoroethylene (PTFE) tubing, 6.35 mm outer diameter/5.80 mm inner diameter (Catalog number 20533) | Sigma-Aldrich Co. LLC, St. Louis, MO |
| PTFE Tube 5239K11 | McMaster-Carr, Elmhurst IL |
| PET film 1 mil | Mitsubishi Polyester Film, Greenville SC |
| 3M Color Coded Flat Cable 3302 Series | 3M Company, St. Paul, MN |
| FPG 50-1NM pulse generator | FID GMBH, Burbach, Germany |
| M100B01353CR1BV Mass Flow Controller | MKS Instruments, Andover, MA |
| CT-AQ8G Ozone generator | Ozonefac Co., Guangdong, China |
| 3M Super Rapid Biological Indicator (SRBI) (Nanosilica-primed polypropylene web) | 3M Company, St. Paul, MN |
| Branson Digital Sonifier | Branson Ultrasonics Co., Danbury, CT |
| Tryptic Soy Agar (TSA) 221283 | Becton Dickinson & Co., Sparks, MD |
| Tryptic Soy Broth (TSB) 297354 | Becton Dickinson & Co., Sparks, MD |
| *Geobacillus stearothermophilus* (ATCC #7953) | iuvo BioScience LLC, Warsaw, New York |
| *Escherichia coli* (ATCC ® 25922) | American Type Culture Collection (ATCC), Manassas, VA |

TABLE 1-continued

Materials

| Materials | Source |
| --- | --- |
| *Pseudomonas aeruginosa* (ATCC ® 15442) | American Type Culture Collection (ATCC), Manassas, VA |
| *Staphylococcus aureus* (ATCC ® 6538) | American Type Culture Collection (ATCC), Manassas, VA |
| *Enterococcus faecalis* (ATCC ® 14506) | American Type Culture Collection (ATCC), Manassas, VA |
| *Clostridium sporogenes* (ATCC ® 3584 ™) | American Type Culture Collection (ATCC), Manassas, VA |
| *Bacillus atrophaeus* (ATCC 9372) | iuvo BioScience, Rush, New York |
| *Mycobacterium smegmatis* (ATCC ® 14468 ™) | American Type Culture Collection (ATCC), Manassas, VA |
| Sterile 1.5-mL centrifuge tubes | USA Scientific, Ocala, FL |
| Sterile 15-mL conical vials | Corning Mexico, Tamaulipas, Mexico |
| Vortex Mixer | Scientific Industries, Bohemia, NY |
| Sterile tweezers | Thermo Fisher Scientific, Waltham, MA |
| Sterile dissecting scissors | Thermo Fisher Scientific, Waltham, MA |
| Razor blades | Stanley Tools, Towson, MD |
| Isopropyl Alcohol | VWR International, Radnor, PA |

Procedures

Preparation of Spore Samples used in the Examples

First, 1×2 cm films of PET were cut and placed in petri dishes. Then, 10 µL of *Geobacillus stearothermophilus* spore solution (~1×10$^8$ Colony Forming Units per mL (CFU/mL), vortexed for 1 minute) were drop-cast onto the films. All spores were kept in a refrigerator at 4° C. between uses. The films containing ~1×10$^6$ spores/film were left to sit with the petri the dish lid open for ≥1 h to ensure that the spore films were fully dry. Next, the films were inserted into 3-inch (7.62 cm) long PTFE sample tubes simulating an endoscope using clean tweezers with 3 films per sample tube. The films were inspected to make sure there was no significant overlap in the spore spot and that the films were in the PTFE tube with the spores face up.

Collection of Spore Samples and Colony Counting in the Examples

After exposure spore films were removed from PTFE sample tubes using sterile tweezers. Then the films were immediately transferred to 50 milliliter (mL) tubes containing 25 mL of 1×phosphate buffered saline (PBST) to neutralize the pH and all charged plasma species. The 1×PBST was prepared from 100 mL of 10×PBS, 900 mL of deionized water and 1 g of polyethylene glycol sorbitan monooleate surfactant commercially available as TWEEN 80 from Sigma-Aldrich of St. Louis, Mo. The 1×PBST solutions were mixed for 5 minutes on a stir plate and were then vacuum filtered with 0.2 micrometer (m) pore size vacuum filter to ensure sterility and stored at 4° C. The spore films in 1×PBST were vortexed, then sonicated for 20 min and vortexed an additional time to ensure all of the spores were removed from the surface.

One mL of the buffer solution containing spores was diluted in Butterfield's buffer. A serial dilution with 10, 100 and 1000-fold reduction in concentration was carried out because the original samples contained 10$^6$ colonies and it was necessary to reduce the concentration enough to count. Then 1 mL of each of the dilution series samples and the original sample in PBST were spread onto disposable spore plates commercially available as PETRIFILM from 3M Company of St. Paul, Minn. The plates were placed onto an aluminum tray and the spores were put in an oven at an optimum growth temperature so that the colonies could grow if CFU were present.

After the spores were incubated, the colony forming units were counted using the PETRIFILM PLATE READER, commercially available from 3M Company. In each case the control samples of untreated spore films were used as the standard. For ideal quantification of kill, the number of CFU per plate was quantified in the range of 20-200. Based on the number of CFU and the known dilution concentration, it was possible to calculate the number of original CFU from the controls or treated spore films and quantify spore kill.

Exemplary Plasma Sterilization Methods

Example 1

A sterilization system generally as described in FIG. 1, and having a plasma generator generally as described in FIG. 2B was provided. More specifically, the plasma generator was constructed by feeding parallel electrodes composed of two strands of 3M Color Coded Flat Cable 3302, commercially available from 3M Company of St. Paul, Minn. into PTFE tubing having an lumen 3/16 inch (4.76 mm) in inside diameter. The anode and cathode were separated on a PVC backing at 0.05 inch (1.27) center-to-center spacing. DC pulsed power was supplied by a power supply commercially available as FPG 50-1NM from FID GmbH of Burbach, Del. The power was set to provide a square pulse with a pulse width of 10 ns and a variable pulse repetition rate and a variable voltage. Power measurements were taken with a homemade E-dot and B-Dot probe.

Flow rates of oxygen and nitrogen gas from tanked sources were controlled using MKS mass flow controllers commercially available from MKS Instruments of Andover, Md. The gasses were mixed and subsequently humidified before being transported to the plasma generator. The plasma byproducts were further transported through connected tubing in order to measure the downstream response. PET film samples which had been inoculated with spores were inserted at recorded lengths within the tubing. In all cases, the spores are downstream from the plasma, outside of the afterglow region. In some cases, the plasma composition was monitored downstream past the spore films using Fourier-Transform Infrared (FTIR) Spectroscopy. An FTIR spectrometer commercially available as NICOLET iS10 from Thermo Scientific of Waltham, Mass., with a 2-meter gas cell was used to make these measurements. In addition, flow rate was monitored using a flow meter to ensure constant gas/plasma flow between experiments. Standard operating conditions are noted in Table 2. In Examples 1-4 below, the standard conditions were used, except where noted. Power was varied by changing both voltage and repetition rate.

TABLE 2

Standard Plasma Sterilization Operating Conditions

| Parameter | Standard Condition |
|---|---|
| Treatment Time | 5 min |
| Voltage | 33 kV |
| Flow Rate | 3 L/min |
| Repetition Rate | 1 kHz |
| Tube Length | 6 ft (about 1.83 m) |
| Tube ID | 0.1875 in (about 4.8 mm) |
| Humidity | 8.3 g/m$^3$ |
| $N_2/O_2$ Ratio | 80% |

In this example, processing parameters, including voltage, repetition rate (pulse repetition frequency, PRF), and gas flow rate were changed independently and the mean $\log_{10}$ of *G. stearothermophilus* was observed and recorded. The parameters were altered independently (all others held constant) of values in Table 1. The process values were then normalized according the equation:

$$s/\text{molecule} = \frac{\frac{V^2}{R} \cdot t_{ON} \cdot PRF}{pQ/RT}$$

The energy term ($V^2/R \, t_{ON}$) was taken from I-V measurements on the device. The process values and results are recorded in Table 3.

TABLE 3

Effect of Plasma Power and Gas Flow Rate

| Flow Rate (Std. L/min) | Power (watts) | Exposure Time (seconds) | Mean Log$_{10}$ (CFU/Sample) | eV/molecule |
|---|---|---|---|---|
| 0 | 0 | 0 | 6.2 | 0.00 |
| 3 | 12 | 300 | 6.1 | 0.06 |
| 3 | 19 | 300 | 5.2 | 0.09 |
| 3 | 38 | 300 | 0.7 | 0.18 |
| 3 | 45 | 300 | 0.0 | 0.21 |
| 3 | 62 | 300 | 0.0 | 0.29 |
| 3 | 8.06 | 300 | 5.5 | 0.04 |
| 3 | 15.5 | 300 | 5.6 | 0.07 |
| 3 | 31 | 300 | 1.0 | 0.14 |
| 3 | 62 | 300 | 0.0 | 0.29 |
| 0.4 | 62 | 300 | 0.0 | 2.16 |
| 0.5 | 62 | 300 | 0.0 | 1.73 |
| 1 | 62 | 300 | 0.0 | 0.86 |
| 2 | 62 | 300 | 0.5 | 0.43 |
| 3 | 62 | 300 | 0.0 | 0.29 |
| 4 | 62 | 300 | 0.0 | 0.22 |
| 6 | 62 | 300 | 0.0 | 0.14 |
| 8 | 62 | 300 | 4.3 | 0.11 |
| 10 | 62 | 300 | 6.2 | 0.09 |

Example 2

The effect of tube volume on kill was investigated by changing the parameter of tube length. All other process parameters were held constant as indicated in Table 1. The results for mean log10 Colony Forming Units (CFU) and the standard deviation (STDEV) about the mean after plasma exposure are recorded in Table 3. A 6-$\log_{10}$ reduction in CFU was observed over the entire range of plasma distance variation from 6 ft. (~1.85 m) to 300 ft (~92.52 m). These distances correspond to post plasma residence times ranging from 0.65 second to 32.5 seconds.

TABLE 4

Effect of Distance from Plasma

| Distance from Plasma (ft) [m] | Mean Log$_{10}$ CFU/Sample | STDEV |
|---|---|---|
| Control | 6.07 | 0.24 |
| 6 [~1.85] | 0 | 0 |
| 12 [~3.71] | 0 | 0 |
| 18 [~5.56] | 0 | 0 |
| 24 [~7.32] | 0 | 0 |
| 36 [~11.10] | 0 | 0 |
| 48 [~14.80] | 0 | 0 |
| 75 [~23.13] | 0 | 0 |
| 100 [~30.84] | 0 | 0 |
| 200 [~61.68] | 0 | 0 |
| 300 [~92.52] | 0 | 0 |

Example 3

In this example, precursors to the plasma were varied independently and the mean $\log_{10}$ CFU and STDEV of *G. stearothermophilus* was observed and recorded. The conditions of Table 2 were used, except that the ratios of nitrogen to oxygen entering the plasma generator were varied. The results of varying nitrogen and oxygen partial pressures are recorded in Table 5.

TABLE 5

Effect of Varying Nitrogen and Oxygen Partial Pressures

| $N_2/N_2 + O_2$ Ratio | Mean Log$_{10}$ (CFU/Sample) | STDEV |
|---|---|---|
| Control | 6.2 | 0.3 |
| 0 | 5.9 | 0.3 |
| 0.2 | 0.0 | 0.0 |
| 0.33 | 0.0 | 0.0 |
| 0.5 | 0.0 | 0.0 |
| 0.66 | 0.0 | 0.0 |
| 0.8 | 0.0 | 0.0 |
| 1 | 3.7 | 0.6 |

Example 4

In this example, water vapor was added to the gas before directing it to the plasma generator in order to vary the humidity of the sterilizing gas. Otherwise, the conditions of Table 2 were used. The effect of varying the humidity of the sterilizing gas on the mean $\log_{10}$ CFU and STDEV are recorded in Table 6.

TABLE 6

Effect of Varying Sterilizing Gas Humidity

| Humidity (g $H_2O/m^3$) | Mean $Log_{10}$ (CFU/Sample) | STDEV |
|---|---|---|
| Control | 6.4 | 0.1 |
| 3.7 | 5.7 | 0.3 |
| 4.1 | 4.7 | 0.4 |
| 4.5 | 4.9 | 1.0 |
| 5.2 | 0.0 | 0.0 |
| 6.6 | 0.0 | 0.0 |
| 8.5 | 0.0 | 0.0 |
| 9.5 | 0.0 | 0.0 |
| 11.4 | 0.0 | 0.0 |

Example 5

A sterilization system generally as described in FIG. 1, and having a plasma generator generally as described in FIG. 2A was provided. More specifically, the ozone generator tube available from Ozonefac Co. (Guangzhou, Guangdong, China) as part of the CT-AQ8G ozone machine was utilized as the plasma electrode. Power was coupled to the plasma electrode from 12 kHz ac power supply with a voltage of 3.6 kV and a total power of 85 W. Oxygen and nitrogen gasses were introduced in the plasma electrode at rates of 0.5 and 2.5 standard liter per minute (SLM), respectively. The gas precursor was humidified with 8.3 g/m³ of vaporized water.

After the plasma generator, the effluent was transported through a 6 foot (~1.83 m) length of PTFE tubing with a ⅛ inch (~3.2 mm) diameter inner lumen. The plasma electrode temperature was varied prior to the start of each recording by wrapping heat tape around the plasma electrode system and controlling the temperature to a predetermined setpoint. The mean number of *G. stearothermophilus* CFU recovered after exposure was observed and recorded. The results are recorded in Table 7.

TABLE 7

Effect of Electrode Temperature

| Electrode Temperature (° F.) [° C.] | Mean $Log_{10}$ (CFU/Sample) Recovered | |
|---|---|---|
| | 120 second Exposure | 300 second Exposure |
| Control | 6.3 | |
| 25 [~−3.9° C.] | 0.0 | 0.0 |
| 75 [~23.9° C.] | 0.0 | 0.0 |
| 100 [~37.8° C.] | 0.0 | 0.0 |
| 125 [~51.7° C.] | 0.0 | 0.0 |
| 150 [~65.6° C.] | 5.0 | 0.0 |
| 175 [~79.4° C.] | 6.3 | 6.0 |

Exemplary Plasma Disinfection Methods for Simulated Endoscope Lumens

The following Examples describe a plasma disinfection method useful to achieve microbial kill of mature biofilm found in lumened medical devices such as endoscopes. The plasma disinfection method provides a 6-log reduction in bacteria after 5 minutes of treatment. The disinfection method works on flexible lumened surfaces such as the interior channels of an endoscope. The disinfection method is effective in the presence of moisture and therefore integrates well in the current reprocessing procedures used to decontaminate endoscopes.

If desired, reprocessed endoscopes that have been manually cleaned can be treated with the plasma disinfection method before they are exposed to a high level of disinfection or even sterilization. Alternatively, high level disinfected scopes can be treated with plasma immediately after the automated endoscope reprocessing (AER) cycle and before storage in a drying cabinet. The scopes can also be manually cleaned, disinfected in an AER cycle and stored in a drying cabinet. Plasma treatment can be applied to the stored scopes on demand in a drying cabinet, e.g., prior to patient use to kill any biofilm that may be growing due to improper storage conditions or in the procedure room before use on a patient similar to flash sterilization.

Plasma disinfection according to the presently disclosed system and method has also been shown to be effective up to a distance of 6 feet from the source of the plasma, which would accommodate a majority of the endoscopes available on the market today. Plasma disinfection is an on-demand point-of-use disinfection system that is portable and scalable to allow for the treatment of multiple endoscopes at one time.

Procedures

Bacterial Culture/Inoculum Preparation

*Pseudomonas aeruginosa* (ATCC 15442) was subcultured on Tryptic Soy Agar (TSA) plates and incubated at 37° C. for 16 to 18 hours. A single colony was isolated from a streak plate and used to inoculate 10 mL of Tryptic Soy Broth bacterial growth media. A culture was grown at 37° C. for 16 to 18 hours. Viable bacterial density was determined by a ten-fold serial dilution which was plated for enumeration. This was used as the inoculum solution to initiate biofilm growth.

Biofilm Growth

Four pieces of PTFE tubing 3.28 feet (~1 m) in length with a 1 mm diameter inner lumen and connector pieces were steam sterilized prior to inoculation. Six hundred microliters of the inoculum were added to fill the entire length of each piece of tubing and biofilm was cultured in each tube for 24 hours at 25° C. The mature biofilm was rinsed with 10% Tryptic Soy Broth Media to remove planktonic (loosely attached) bacteria for 48 hours. One of the 4 pieces of PTFE tubing was used as a positive control sample to determine the growth of biofilm in the non-disinfected lumens.

Biofilm Growth Assessment

The positive control PTFE tubing was cut into halves. One half was further cut into four 10 cm sections representing the ends and the middle of the lumen. Each tubing section was placed into a separate sterile Falcon tube containing 15 mL of phosphate buffered saline. The samples were sonicated for 20 minutes at 25° C. The sonicated samples were vortexed and a tenfold serial dilution was made of the PBST used to sonicate each tubing section by transferring 1 mL of the liquid to a sterile conical vial containing 9 mL buffered water.

Dilutions were plated on TSA to determine the population present in the biofilm. The TSA plates were incubated at 23° C.+/−2° C. for a total of 72 hours. The mean population of *Pseudomonas aeruginosa* (CFU/cm$^2$) present in the mature biofilm was determined and is presented in Table 8.

TABLE 8

Mean population of *Pseudomonas aeruginosa* (CFU/cm$^2$) Present in Mature Biofilm

| Test Organism | Sample # | Recovered (CFU) in Test Control | Section of the Lumen Tested | Mean Population (CFU/cm$^2$) |
|---|---|---|---|---|
| Pseudomonas aeruginosa (ATCC 15442) | 1 | 2.40E+08 | Front | 2.34E+09 |
| | 2 | 2.46E+08 | Middle #1 | |
| | 3 | 1.85E+08 | Middle #2 | |
| | 4 | 1.19E+08 | End | |

Example 6

Treatment of Polytetrafluoroethylene (PTFE) Tubing Containing Biofilm

A sterilization system generally as described in FIG. 1, and having a plasma generator generally as described in FIG. 2B was provided. More specifically, the plasma generator was constructed by feeding parallel electrodes composed of two strands of 3M Color Coded Flat Cable 3302, commercially available from 3M Company (St. Paul, Minn.) into PTFE tubing having an lumen 3/16 inch (4.76 mm) in inside diameter. The anode and cathode were separated on a PVC backing at a 0.05 inch (1.27 cm) center-to-center spacing.

DC pulsed power was supplied by a power supply commercially available as FPG 50-1NM from FID GmbH (Burbach, Germany). The power was set to provide a rectangular pulse with a pulse width of 10 nanoseconds and a variable pulse repetition rate and a variable voltage. Power measurements were taken with a homemade E-dot and B-dot probe.

The flow rate of compressed air or a nitrogen/oxygen mixture into the was controlled using an MKS mass flow controller commercially available from MKS Instruments of Andover, Md. The gas was humidified through a bubbling unit before being transported to the plasma generator. The plasma byproducts were further transported through connected tubing in order to measure the downstream response. The remaining 3 pieces of PTFE tubing inoculated with biofilm were PTFE tubing connected using standard tubing adapters 6 feet (~1.83 m) downstream from the plasma generator described in Example 1. The operating parameters are recorded below in Table 9.

TABLE 9

Standard Plasma Disinfection Operating Conditions

| Parameter | Standard Condition |
|---|---|
| Treatment Time | 5 min |
| Voltage | 33 kV |
| Flow Rate | 2 L/min |
| Repetition Rate | 1 kHz |
| Tube Length | 6 ft (~1.83 m) |
| Tube ID | 0.1875 in (~4.8 mm) |
| Gas Temperature | 70° F. (~21.1° C.) |
| Humidity | 100% RH |

The PTFE biofilm tubes contained rinse liquid, which was subsequently blown out of the lumen once the plasma treatment was initiated. This liquid is recorded as the "flow though sample," and was evaluated by vacuum filtration to determine if any bacteria could be recovered. No bacteria were present in the "flow through sample."

After plasma treatment, the PTFE tubing was flushed with PBST (1 ml×4) to remove any remaining bacteria which was subsequently recovered by vacuum filtration. Colony forming units counted from this liquid were recorded as "filtrate from wash." The washed tubing was then cut into sections, placed in a sterile bottle containing 200 mL of PBST and sonicated for 20 mins at 25° C. to remove any biofilm from the lumen of the tubing section. The bacteria present in the sonicated solution was then recovered using vacuum filtration.

The recovered colony forming units after exposure to the plasma are recorded in Table 10. No bacteria were recovered from the "flow through sample," the "filtrate from wash," or from the tubing pieces after plasma treatment. Full kill of Pseudomonas aeruginosa present in a mature biofilm (2.34× 10$^9$ CFU/cm$^2$) was observed after plasma exposure for 5 mins.

TABLE 10

Post Plasma Disinfection Biofilm Recovery

| Sample # | Sample Type | CFU Recovered - Mean CFU (CFU/cm$^2$) |
|---|---|---|
| Lumen #1 | Flow through sample | 0 CFU - 2.34E+09 CFU/cm$^2$ |
| | Filtrate from wash | 0 CFU - 2.34E+09 CFU/cm$^2$ |
| | Recovery from sonicated lumen pieces | 0 CFU - 2.34E+09 CFU/cm$^2$ |
| Lumen #2 | Flow through sample | 0 CFU - 2.34E+09 CFU/cm$^2$ |
| | Filtrate from wash | 0 CFU - 2.34E+09 CFU/cm$^2$ |
| | Recovery from sonicated lumen pieces | 0 CFU - 2.34E+09 CFU/cm$^2$ |
| Lumen #3 | Flow through sample | 0 CFU - 2.34E+09 CFU/cm$^2$ |
| | Filtrate from wash | 0 CFU - 2.34E+09 CFU/cm$^2$ |
| | Recovery from sonicated lumen pieces | 0 CFU - 2.34E+09 CFU/cm$^2$ |
| Lumen #4 | Flow through sample | 0 CFU - 2.34E+09 CFU/cm$^2$ |
| | Filtrate from wash | 0 CFU - 2.34E+09 CFU/cm$^2$ |
| | Recovery from sonicated lumen pieces | 0 CFU - 2.34E+09 CFU/cm$^2$ |
| Lumen #5 | Flow through sample | 0 CFU - 2.34E+09 CFU/cm$^2$ |
| | Filtrate from wash | 0 CFU - 2.34E+09 CFU/cm$^2$ |
| | Recovery from sonicated lumen pieces | 0 CFU - 2.34E+09 CFU/cm$^2$ |
| Lumen #6 | Flow through sample | 0 CFU - 2.34E+09 CFU/cm$^2$ |
| | Filtrate from wash | 0 CFU - 2.34E+09 CFU/cm$^2$ |
| | Recovery from sonicated lumen pieces | 0 CFU - 2.34E+09 CFU/cm$^2$ |

Exemplary Plasma Disinfection Methods for Washed/Undried Lumens

The following Examples describe a plasma disinfection method useful to achieve microbial kill of biofilm found in washed but undried lumened medical devices such as endoscopes. The Examples show effective kill of four different microorganisms in liquid droplets using two models (10 μL wells and 5.80 mm ID lumens) treated using a remote plasma treatment system and method. These Examples demonstrate disinfection-level kill (≥6 log$_{10}$) using models that mimic the conditions and residual droplets encountered in the channels of a washed flexible endoscope. This remote plasma system and method is effective at killing microorganisms at a distance of 10 feet (~3 m) away from the plasma source using an extremely short treatment cycle (e.g., 60-150 seconds).

Procedures

Bacterial Culture

Individual streak plates (TSA) of each organism (*E. coli, P. aeruginosa, S. aureus,* and *E. faecalis*) were prepared from freezer stocks and incubated for 24 hours at 37° C. A single colony from each plate was used to inoculate 10 mL of TSB growth medium to culture each organism overnight (16-18 hours) with shaking at 250 RPM at 37° C. Each overnight culture reached a concentration ~10$^9$ colony forming units per milliliter (CFU/mL) and was diluted 1:10 in Butterfield's Buffer to create a solution containing ~10$^8$ CFU/mL used to inoculate samples for plasma treatment.

Plasma Exposure

A plasma disinfection system generally as described in FIG. 1, and having a plasma generator generally as described in FIG. 2A was utilized in examples 7 and 8. Specifically, the ozone generator tube available from Ozonefac Co. (Guangzhou, Guangdong, China) as part of the CT-AQ8G ozone machine was utilized as the plasma electrode. Power was coupled to the plasma electrode from 12 kHz ac power supply with a voltage of 3.6 kV and a total power of 85 W.

Plasma disinfection was achieved by transporting the gas output from the plasma through a 10-foot (~3 m) length of FEP tubing with an inner diameter of ⅛ inch (~3.2 mm). Samples were inserted at the end of the 10-foot (~3 m) tube. The gas output from the remote plasma generator was flowing at a rate of 3 L/min, and the gas was selected to be 1,000 standard cm3/min (SCCM) of moist air and 2000 SCCM of dry air. The relative humidity during all disinfection treatments ranged between 40-60%.

The disinfection treatment cycle for the SRBI wells described in Example 7 consisted of a 150 second plasma exposure followed by a 60 second air flush. Plasma treatments in the Lumen Model (Example 8) ranged from 0-150 seconds followed by a 60 second air flush.

SRBI Well Sample Preparation

3M SRBI nanosilica primed wells were cut from a roll of the film into individual strips using a standard paper cutter. Each strip contained eight wells capable of holding 10 μL of liquid between the two edges. The strips were cleaned by wiping with 70% isopropyl alcohol and dried prior to use. For each experiment, ~10$^6$ microorganisms were loaded into wells in positions 1 and 8 by pipetting 10 μL of a bacterial suspension containing ~10$^8$ CFU/mL prepared for each organism (*E. coli, P. aeruginosa, S. aureus* and *E. faecalis*) as described in the Bacterial Culture section.

For plasma experiments, strips containing the microbial samples were loaded into the 1 foot removable section 6.35 mm outer diameter (OD)/5.80 mm inner diameter (ID) PTFE tubing using sterile tweezers and either treated with a plasma cycle of 150 seconds +60 seconds of air or 210 seconds of air (positive controls). After the plasma exposure, the wells containing the 10 μL samples were cut off from the rest of the strip using sterile dissecting scissors and transferred to individual 1.5-mL tubes containing 1 mL of PBS-TWEEN with sterile tweezers. Each tube was vortex-mixed at maximum speed for 1 minute and serial dilutions were made in Butterfield's Buffer, which were plated on PETRIFILM AEROBIC COUNT plates through the 10$^{-7}$ dilution for each sample.

Inoculated plates were incubated for 24-48 hours at 37° C. and counted using a 3M PETRIFILM READER. The 1 minute vortex-mixing in PBS-TWEEN was validated by comparing recovery to enumeration controls (direct serial dilutions of the 10 μL inoculum into Butterfield's Buffer instead of the SRBI well; see Table 11), thereby confirming that this method recovered all of the microorganisms deposited in the SRBI well. For each data point, n=6.

TABLE 11

SRBI Well Sample Recovery Method (1 Minute Vortex) Validation

| Microorganism | Inoculum (CFU) | Recovered (CFU) | Percent Recovery |
|---|---|---|---|
| *E coli* | 2.68E+06 | 2.63E+06 | 98 |
| *P. aeruginosa* | 1.63E+06 | 1.60E+06 | 98 |
| *S. aureus* | 1.83E+06 | 2.30E+06 | 126 |
| *E. faecalis* | 1.48E+06 | 1.41E+06 | 95 |

PTFE Lumen Model Sample Preparation 6.35 mm OD/5.80 mm ID PTFE tubing was cut into 6" lumen sections and steam sterilized prior to use. Samples were inoculated by pipetting 250 μL of a *P. aeruginosa* culture containing ~10$^8$ CFU/mL into the PTFE lumen. The sample was tilted and rolled to spread the bacteria throughout the tube.

The lumens were incubated at room temperature (~25° C.) for 30 minutes, then most of the liquid (~150-200 μL) was removed and collected by holding the lumen over a 15-mL conical vial. After this process was completed, visible droplets (~5-50 μL in volume) still remained in the tube.

The inoculated lumens were then attached to the plasma treatment set up as described in the Plasma Exposure section above. Each removable section of tubing was sequentially connected to the 10-foot (~3 m) piece. A time-course experiment was conducted with duplicate samples exposed to a plasma disinfection treatment cycle of 0 seconds, 15 seconds, 30 seconds, 60 seconds, 90 seconds, 120 seconds and 150 seconds, with each plasma exposure followed by a 60 second air flush.

After each disinfection treatment cycle was complete, each lumen was cut in half to create two 3-inch (~7.62 cm) sections using a razor blade freshly cleaned with isopropyl alcohol and transferred to a 15-mL conical vial containing 10 mL of PBS-TWEEN. Any remaining viable bacteria were then recovered from each lumen by vortex-mixing the vial at maximum speed for 1 minute, disrupting with 2×20 second duration pulses at 20 kHz with a probe sonicator set at 39% of the maximum amplitude, then vortex-mixing again for 1 minute at maximum speed.

Serial dilutions of each tube were made in Butterfield's Buffer and plated on PETRIFILM AEROBIC COUNT plates through the $10^{-7}$ dilution for each sample (with the original 10 mL recovery solution being the $10^{-1}$ dilution). The inoculated plates were incubated for 24-48 hours at 37° C. and counted using a 3M PETRIFILM READER. This lumen test procedure was adapted from the American Society for Testing and Materials International (ASTM) method E1837—Standard Test Method to Determine Efficacy of Disinfection Processes for Reusable Medical Devices (Simulated Use Test).

Example 7

Bacterial Kill from 150 sec Plasma Treatment in Liquid Droplets in 10 µL Wells

Six replicate samples of each microorganism were exposed to a 150 second duration plasma treatment and a 60 second duration air purge at a flow rate of 3 L/min at a distance to 10 feet (~3 m) away from the plasma source. Each sample contained ~$10^6$ viable cells in 10 µL of liquid when the plasma treatment began.

Measuring the mass of the SRBI strips before and after plasma the treatment cycle revealed that a mean of 0.0011 g (~1.1 µL) of the 10 µL droplet (n=24) evaporated during the plasma exposure (data not shown). After the plasma cycle, no viable colony forming units were recovered from the samples exposed to plasma, and full kill (6+logs; Table 12) was achieved for all four microorganisms tested (E. coli, P. aeruginosa, S. aureus and E. faecalis). These four organisms were chosen as representative examples of both Gram-negative and Gram-positive bacteria and due to their relevance as organisms of "high concern" for endoscope reprocessing as stated by the Centers for Disease Control and Prevention (CDC). (see, e.g., "Interim Protocol for Healthcare Facilities Regarding Surveillance for Bacterial Contamination of Duodenoscopes after Reprocessing" which can be found on the CDC website (https://www.cdc.gov/hai/pdfs/cre/interim-duodenoscope-surveillance-Protocol.pdf; published Mar. 11, 2015, last accessed Jun. 12, 2017). For each data point, the number of samples n=6.

TABLE 12

Bacterial Kill from 150 second Plasma Treatment in 10 µL Wells

| Microorganism | No Plasma Positive Control (Mean Recovered CFU) | 150 seconds Plasma Treatment (Mean Recovered CFU) | $Log_{10}$ Reduction |
|---|---|---|---|
| E. coli | 6.76E+06 | 0.00E+00 | 6.83 |
| P. aeruginosa | 1.48E+06 | 0.00E+00 | 6.17 |
| S. aureus | 5.89E+06 | 0.00E+00 | 6.77 |
| E. faecalis | 1.29E+06 | 0.00E+00 | 6.11 |

Example 8

Bacterial Kill Curve in Liquid Droplets in PTFE Lumens

A kill curve in a 5.80 mm ID PTFE lumen model based on ASTM E1837 was generated by exposing duplicate samples incubated with P. aeruginosa suspensions to plasma cycles of varying exposure time from 0 second-150 seconds. Each lumen contained droplets ranging from ~5-50 µL when plasma treatment was initiated. Visible droplets remained in the lumen after plasma exposure, but the amount of residual liquid was not quantified. Recovery of any remaining viable bacteria after the plasma cycle showed the complete kill (7.6-$log_{10}$) was achieved within 60 seconds of plasma treatment (Table 13).

TABLE 13

Survival of P. aeruginosa in a 5.80 mm ID Lumen over Time.

| Exposure time (sec) | Mean Recovered CFU/sample (n = 2) |
|---|---|
| 0 | 3.87E+07 |
| 15 | 2.85E+05 |
| 30 | 2.10E+02 |
| 60 | 0.00E+00 |
| 90 | 0.00E+00 |
| 120 | 0.00E+00 |
| 150 | 0.00E+00 |

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus the appearances of the phrases such as "in one or more embodiments," "in certain embodiments," "in one embodiment" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

Furthermore, all publications and patents referenced herein are incorporated by reference in their entirety to the same extent as if each individual publication or patent was specifically and individually indicated to be incorporated by reference. Various exemplary embodiments have been described.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. These and other embodiments are within the scope of the following claims.

The invention claimed is:

1. A system, comprising:
   a plasma generator including:
      an electrode,
      a shield, and
      a dielectric gap between the electrode and the shield;
   a source of electrical power connected to the plasma generator, for applying an electrode energy density between the electrode and the shield;
   a source of a gas comprising water vapor, oxygen, and nitrogen, configured to provide a flow of the gas through the plasma generator between the electrode and the shield to form a plasma containing acidic species from the gas; and
   a filter for removing the acidic species from the gas, wherein the filter comprises one or more adsorbent or absorbent materials selected from activated carbon, a chemical species with a basic functionality, a basic ion exchange resin, a reducing species selected from one or more active metals selected from platinum and palladium; and a molecular sieve,
wherein a temperature at the surface of the shield is maintained at less than 150° C. when the electrode energy density is greater than 0.05 eV/molecule of the gas passing between the electrode and the shield, optionally wherein the system further comprises a device for conveying an article undergoing sterilization through a chamber fluently connected to the flow of the gas through the plasma generator containing the acidic and/or oxidizing species.

2. The system of claim 1, wherein the gas includes one or more species selected from the group consisting of molecular oxygen, molecular nitrogen, nitric oxide, nitric acid, and nitrous oxide.

3. The system of claim 2, wherein the gas comprises air, optionally wherein a relative humidity of the gas entering the plasma generator is at least 21%.

4. The system of claim 1, further comprising a cooling apparatus.

5. A method of sterilizing a contaminated article, comprising:
   providing a sterilizer including:
      a plasma generator having:
         an electrode,
         a shield, and
         a dielectric gap between the electrode and the shield;
      a source of electrical power connected to the plasma generator for applying
      an electrode energy density between the electrode and the shield; and
      a source of a gas comprising water vapor, oxygen, and nitrogen, configured
      to provide a flow of the gas through the plasma generator between the electrode and the shield to form a plasma containing acidic and/or oxidizing species from the gas;
   providing the flow of the gas through the plasma generator between the electrode and the shield to form the plasma containing the acidic and/or oxidizing species from the gas, wherein a temperature at the surface of the shield is maintained at less than 150° C. when the electrode energy density is greater than 0.05 eV/molecule of the gas passing between the electrode and the shield;
   directing the gas containing the acidic and/or oxidizing species from the plasma generator into an enclosed area enclosing at least a portion of the article undergoing sterilization to achieve a desired degree of sterilization of the article; and
   exposing the contaminated article to the gas containing the acidic and/or oxidizing species for a time sufficient to sterilize the contaminated article, optionally wherein the time sufficient to sterilize the article is no greater than one hour.

6. The method of claim 5, further comprising removing at least a portion of the acidic and/or oxidizing species from the gas upon achieving the desired degree of sterilization of the article.

7. The method of claim 6, wherein the removing at least a portion of the acidic and/or oxidizing species from the gas is performed with an apparatus comprising one or more materials selected from the group consisting of activated carbon, a species with a basic functionality, a species providing a basic adsorbent, a reducing species, and a molecular sieve.

8. The method of claim 5, wherein the enclosed area is a sterilization chamber.

9. The method of claim 5, wherein the article undergoing sterilization is a medical device and the enclosed area is a hollow area of the medical device.

10. The method of claim 9, wherein the medical device is an endoscope and the hollow area is a lumen of the endoscope, further wherein the gas containing the acidic and/or oxidizing species from the plasma generator is passed through the lumen of the endoscope.

11. The method of claim 9, wherein the medical device is a medical instrument and the hollow area is at least one internal cavity of the medical instrument.

12. The method of claim 5, wherein the gas includes one or species selected from the group consisting of molecular oxygen, molecular nitrogen, nitric oxide, nitric acid, and nitrous oxide.

13. A method of disinfecting a contaminated article, comprising:
   providing a disinfecting system including:
      a plasma generator having
         an electrode,
         a shield, and
         a dielectric gap between the electrode and the shield,
      a source of electrical power connected to the plasma generator for applying an electrode energy density between the electrode and the shield, and
      a source of a gas comprising water vapor, oxygen, and nitrogen, configured to provide a flow of the gas through the plasma generator between the electrode and the shield to form a plasma containing acidic and/or oxidizing species from the gas, wherein the temperature at a surface of the shield is maintained at less than 150° C. when the electrode energy density is greater than 0.05 eV/molecule of the gas passing between the electrode and the shield,
   providing the flow of the gas through the plasma generator between the electrode and the shield to form the plasma containing the acidic and/or oxidizing species from the gas;
   directing the gas containing the acidic and/or oxidizing species from the plasma generator into an enclosed area enclosing at least a portion of the contaminated article, wherein the contaminated article is contaminated with at least one of a bio-film comprising a plurality of microorganisms, or a plurality of microbial or fungal spores; and
   exposing the contaminated article to the gas containing the acidic and/or oxidizing species for an exposure time sufficient to disinfect the contaminated article by achieving at least a 2-$\log_{10}$ and optionally up to an 11-$\log_{10}$ reduction in colony forming units of the disinfected contaminated article relative to the contaminated article.

14. The method of claim 13, wherein the contaminated article is a medical device and the enclosed area is a hollow area of the medical device.

15. The method of claim 14, wherein the medical device is an endoscope and the hollow area is a lumen of the endoscope, further wherein the gas containing the acidic and/or oxidizing species from the plasma generator is passed through the lumen of the endoscope.

16. The method of claim 13, wherein the bio-film comprises a plurality of microorganisms selected from the group consisting of *Geobacillus stearothermophilus, Bacillus subtilis, Bacillus atrophaeus, Bacillus megaterium, Bacillus coagulans, Clostridium sporogenes, Bacillus pumilus, Aspergillus brasiliensis, Aspergillus oryzae, Aspergillus niger, Aspergillus nidulans, Aspergillus flavus, Clostridium difficile, Mycobacterium terrae, Mycobacterium tuberculosis, Mycobacterium bovis, Escherichia colt, Staphylococcus aureus, Pseudomonas aeruginosa, Staphylococcus epidermidis, Staphyolococcus lugdunensis, Staphylococcus saprophyticus, Enterococcus faecium, Enterococcus faecalis, Propionobacterium acnes, Klebsiella pneumoniae, Enterobacter cloacae, Proteus mirabilus, Salmonella enterica, Salmonella typhi, Shigella flexiniri*, and combinations thereof.

17. The method of claim 13, wherein the contaminated article is contaminated with a bio-film comprising a plurality of microorganisms, further wherein the exposure time is at least 5 minutes, and the reduction in colony forming units of the disinfected article relative to the contaminated article is from 4-$\log_{10}$ to 9-$\log_{10}$, optionally wherein the exposure time is at most one hour.

18. The method of claim 13, wherein the contaminated article is contaminated with a bio-film comprising a plurality of microbial or fungal spores, further wherein the exposure time is at least 2 minutes, and the reduction in colony forming units of the disinfected article relative to the contaminated article is from 6-$\log_{10}$ to 10-$\log_{10}$, optionally wherein the exposure time is at most one hour.

* * * * *

UNITED STATES PATENT AND TRADEMARK OFFICE
CERTIFICATE OF CORRECTION

PATENT NO. : 10,933,151 B2
APPLICATION NO. : 16/307302
DATED : March 2, 2021
INVENTOR(S) : Caleb Nelson It is certified that error appears in the above-identified patent and that said Letters Patent is hereby corrected as shown below:

On the Title Page

Column 2
Line 4, item [56] Delete "Dieletric" and insert -- Dielectric --, therefor.

In the Specification

Column 1
Line 27, Delete "modem" and insert -- modern --, therefor.

Column 4
Line 29, Before "Embodiment" delete "claim".
Line 33, Delete "species" and insert -- more species --, therefor.

Column 5
Line 29, Delete "Staphyolococcus" and insert -- Staphylococcus --, therefor.
Line 31, Delete "Propionobacterium" and insert -- Propionibacterium --, therefor.
Line 33, Delete "mirabilus," and insert -- mirabilis, --, therefor.
Line 34, Delete "flexiniri," and insert -- flexneri, --, therefor.

Column 11
Line 3, Delete "Staphyolcoccus" and insert -- Staphylococcus --, therefor.
Line 5, Delete "Propionobacterium" and insert -- Propionibacterium --, therefor.
Line 7, Delete "mrabilus," and insert -- mirabilis, --, therefor.
Line 8, Delete "flexiniri;" and insert -- flexneri; --, therefor.
Line 28, Delete "minute" and insert -- minute. --, therefor.
Line 37, Delete "to10-" and insert -- to 10- --, therefor.

Column 12
Line 7, Delete "minute" and insert -- minute. --, therefor.

Signed and Sealed this
Twenty-fifth Day of June, 2024

Katherine Kelly Vidal
*Director of the United States Patent and Trademark Office*

CERTIFICATE OF CORRECTION (continued)
U.S. Pat. No. 10,933,151 B2

Column 13
Line 51, Delete "(m)" and insert -- (μm) --, therefor.

Column 17
Line 50 (approx.), Delete "[~-3.9° C.}" and insert -- [~-3.9° C.] --, therefor.
Line 52 (approx.), Delete "[~23.9° C.}" and insert -- [~23.9° C.] --, therefor.
Line 54 (approx.), Delete "[~37.8° C.}" and insert -- [~37.8° C.] --, therefor.
Line 56 (approx.), Delete "[~51.7° C.}" and insert -- [~51.7° C.] --, therefor.
Line 58 (approx.), Delete "[~65.6° C.}" and insert -- [~65.6° C.] --, therefor.
Line 60 (approx.), Delete "[~79.4° C.}" and insert -- [~79.4° C.] --, therefor.

Column 18
Line 41, Delete "biofilm." and insert -- biofilm --, therefor.

In the Claims

Column 26
Line 18, Claim 12, delete "species" and insert -- more species --, therefor.

Column 27
Line 7, Claim 16, delete "colt," and insert -- coli, --, therefor.
Line 9, Claim 16, delete "Staphyolococcus" and insert -- Staphylococcus --, therefor.
Lines 10-11, Claim 16, delete "Propionobacterium" and insert -- Propionibacterium --, therefor.
Line 12, Claim 16, delete "mirabilus," and insert -- mirabilis, --, therefor.
Line 13, Claim 16, delete "flexiniri," and insert -- flexneri, --, therefor.